(12) United States Patent
Fefer

(10) Patent No.: US 8,747,874 B2
(45) Date of Patent: Jun. 10, 2014

(54) SPRAY OIL AND METHOD OF USE THEREOF FOR CONTROLLING TURFGRASS PESTS

(75) Inventor: Michael Fefer, Whitby (CA)

(73) Assignee: Suncor Energy Inc., Calgary, Alberta (CA)

(*) Notice: Subject to any disclaimer, the term of this patent is extended or adjusted under 35 U.S.C. 154(b) by 278 days.

(21) Appl. No.: 12/563,929

(22) Filed: Sep. 21, 2009

(65) Prior Publication Data

US 2010/0016447 A1 Jan. 21, 2010

Related U.S. Application Data

(62) Division of application No. 10/908,538, filed on May 16, 2005, now abandoned.

(60) Provisional application No. 60/572,544, filed on May 18, 2004.

(51) Int. Cl.
*A01N 25/32* (2006.01)

(52) U.S. Cl.
USPC .......................................... 424/406; 424/405

(58) Field of Classification Search
None
See application file for complete search history.

(56) References Cited

U.S. PATENT DOCUMENTS

| 2,714,062 A | 7/1955 | Lockrey |
| 2,786,821 A | 3/1957 | Gardner |
| 2,870,037 A | 1/1959 | Converse |
| 3,131,119 A | 4/1964 | Fordyce |
| 3,615,799 A | 10/1971 | Gannon |
| 3,689,574 A | 9/1972 | Engelhart |
| 3,950,265 A | 4/1976 | Albrecht |
| 3,997,322 A | 12/1976 | Ratledge |
| 4,015,970 A | 4/1977 | Hennart |
| 4,094,845 A | 6/1978 | De Long |
| 4,124,720 A | 11/1978 | Wenmaekers |
| 4,431,554 A | 2/1984 | Baur |
| 4,698,334 A | 10/1987 | Horriere |
| 4,734,432 A | 3/1988 | Szego et al. |
| 4,761,423 A | 8/1988 | Szego |
| 4,826,863 A | 5/1989 | Szego et al. |
| 4,834,908 A | 5/1989 | Hazen |
| 4,853,026 A | 8/1989 | Frisch |
| 4,902,333 A | 2/1990 | Quimby |
| 4,971,840 A | 11/1990 | Boho |
| 5,084,087 A | 1/1992 | Hazen |
| 5,102,442 A | 4/1992 | Hazen |
| 5,137,726 A | 8/1992 | Ogawa et al. |
| 5,178,795 A * | 1/1993 | Roberts .......................... 516/57 |
| 5,229,356 A | 7/1993 | Tocker |
| 5,238,604 A | 8/1993 | Hazen |
| 5,308,827 A | 5/1994 | Sakamoto |
| 5,336,661 A | 8/1994 | Lucas |
| 5,393,791 A | 2/1995 | Roberts |
| 5,409,885 A | 4/1995 | Derian |
| 5,504,054 A | 4/1996 | Murphy |
| 5,547,918 A | 8/1996 | Newton |
| 5,580,567 A | 12/1996 | Roberts |
| 5,599,768 A | 2/1997 | Hermansky |
| 5,599,804 A | 2/1997 | Mudge |
| 5,643,852 A | 7/1997 | Lucas |
| 5,658,851 A | 8/1997 | Murphy et al. |
| 5,665,672 A | 9/1997 | Lucas |
| 5,703,016 A | 12/1997 | Magin |
| 5,739,371 A | 4/1998 | O'Lenick |
| 5,741,502 A | 4/1998 | Roberts |
| 5,958,104 A * | 9/1999 | Nonomura et al. ............... 71/11 |
| 6,033,647 A | 3/2000 | Touzan |
| 6,117,820 A | 9/2000 | Cutler |
| 6,146,652 A | 11/2000 | Gore |
| 6,159,900 A | 12/2000 | Bieringer |
| 6,210,656 B1 | 4/2001 | Touzan |
| 6,221,811 B1 | 4/2001 | Policello |

(Continued)

FOREIGN PATENT DOCUMENTS

| CA | 964482 | 3/1975 |
| CA | 2069311 | 4/1991 |
| CA | 2434848 | 8/2002 |
| CA | 2496142 | 8/2005 |
| CA | 2562718 | 4/2008 |
| CA | 2605092 | 4/2008 |
| DE | 2511077 | 9/1976 |
| EP | 0498231 | 8/1992 |
| EP | 0598515 | 5/1994 |
| EP | 0862857 | 9/1998 |

(Continued)

OTHER PUBLICATIONS

Bakke, Analysis of Issues Surrounding the Use of Spray Adjuvants With Herbicides, 2002.
Blenis et al, Evaluation of Fungicides and Surfactants for Control of Fairy Rings Caused by *Marasmius oreades* (Bolt ex. Fr.) Fr., HortScience, 1997, 1077-1084, 32(6).
Burpee et al., Interactive Effects of Plant Growth Regulators and Fungicides on Epidemics of Dollar Spot in Creeping Bentgrass, Plant Disease, 1996, 1245-1250, 80(11).

(Continued)

*Primary Examiner* — Neil Levy
(74) *Attorney, Agent, or Firm* — Fish & Richardson P.C.

(57) ABSTRACT

A paraffinic spray oil and a method of using the spray oil for controlling turfgrass pests is disclosed. The spray oil comprises paraffinic oil and a quick break emulsifier, which is formulated as an oil-in-water (O/W) emulsion for use. The paraffinic oil and emulsifier are present in a weight ratio ranging from about 95:5 to about 99.95:0.05, and preferably from about 98.5:1.5 to about 99.9:0.1. When applied to turfgrass, the O/W emulsion quickly releases the oil phase upon application to the turfgrass to contact pests thereon. When provided at sufficient paraffinic oil dosages, generally at least about 0.5 gal oil/acre and preferably in the range of about 0.5 gal/acre to about 60 gal/acre, the spray oil is effective in controlling a variety of turfgrass pests, particularly insect and fungal pests, with little or no phytotoxic effects. Further, use of the spray oil as indicated for controlling turfgrass pests also enhances the growth of turfgrass.

31 Claims, No Drawings

(56) References Cited

U.S. PATENT DOCUMENTS

| | | |
|---|---|---|
| 6,329,321 B2 | 12/2001 | Okura |
| 6,403,061 B1 | 6/2002 | Candau |
| 6,416,748 B1 | 7/2002 | Candau |
| 6,432,877 B2 | 8/2002 | Okura |
| 6,515,031 B2 | 2/2003 | Fefer |
| 6,673,360 B2 | 1/2004 | Fefer |
| 6,683,030 B2 | 1/2004 | Kober et al. |
| 6,713,518 B1 | 3/2004 | Bessette et al. |
| 6,734,202 B2 | 5/2004 | Cotter |
| 6,803,345 B2 | 10/2004 | Herold |
| 6,878,674 B2 | 4/2005 | Kobayashi |
| 7,799,343 B2 | 9/2010 | Loughner |
| 2001/0019728 A1 | 9/2001 | Basinger |
| 2003/0087764 A1 | 5/2003 | Pallas |
| 2003/0194454 A1 | 10/2003 | Bessette et al. |
| 2003/0198659 A1 | 10/2003 | Hoffmann |
| 2003/0198696 A1 | 10/2003 | Keen |
| 2004/0132621 A1 | 7/2004 | Frisch |
| 2004/0167034 A1 | 8/2004 | Coote |
| 2005/0026786 A1 | 2/2005 | Deckwer |
| 2005/0181949 A1 | 8/2005 | Norton |
| 2005/0202102 A1 | 9/2005 | Miller |
| 2005/0233907 A1 | 10/2005 | Nabors |
| 2005/0274164 A1 | 12/2005 | Coates |
| 2006/0063676 A1 | 3/2006 | Brigance |
| 2006/0068991 A1 | 3/2006 | Norton |
| 2006/0276339 A1 | 12/2006 | Windsor |
| 2006/0282961 A1 | 12/2006 | Hughes |
| 2006/0293188 A1 | 12/2006 | Norton |
| 2007/0184005 A1 | 8/2007 | Policello |
| 2008/0085832 A1 | 4/2008 | Fefer |
| 2008/0112909 A1 | 5/2008 | Faler |
| 2008/0153702 A1 | 6/2008 | Voeste |
| 2008/0161367 A1 | 7/2008 | Voeste |
| 2008/0280763 A1 | 11/2008 | Hodge |
| 2009/0325922 A1 | 12/2009 | Fefer |

FOREIGN PATENT DOCUMENTS

| | | |
|---|---|---|
| EP | 1173059 | 11/2000 |
| GB | 745360 | 2/1956 |
| GB | 747909 | 4/1956 |
| GB | 748422 | 5/1956 |
| GB | 753976 | 8/1956 |
| GB | 758926 | 10/1956 |
| GB | 762866 | 12/1956 |
| GB | 763246 | 12/1956 |
| GB | 765459 | 1/1957 |
| GB | 792045 | 3/1958 |
| GB | 1044895 | 10/1966 |
| GB | 1249674 | 10/1971 |
| GB | 1417364 | 12/1975 |
| GB | 2123819 | 2/1984 |
| GB | 2176493 | 12/1986 |
| JP | 57028184 | 2/1982 |
| JP | 2138376 | 5/1990 |
| JP | 3183505 | 8/1991 |
| JP | 3221576 | 9/1991 |
| JP | 4128003 | 4/1992 |
| JP | 8218225 | 8/1996 |
| JP | 11137084 | 5/1999 |
| WO | 9007272 | 7/1990 |
| WO | 9632010 | 10/1996 |
| WO | 9632011 | 10/1996 |
| WO | 9835561 | 8/1998 |
| WO | 0221913 | 3/2002 |
| WO | 02089573 | 11/2002 |
| WO | 02096199 | 12/2002 |
| WO | 03101195 | 12/2003 |
| WO | 03105587 | 12/2003 |
| WO | 2004030641 | 4/2004 |
| WO | 2004080177 | 9/2004 |
| WO | 2005009132 | 2/2005 |
| WO | 2005055716 | 6/2005 |
| WO | 2007117720 | 10/2007 |
| WO | 2007136597 | 11/2007 |
| WO | 2008049192 | 5/2008 |
| WO | 2008073397 | 6/2008 |
| WO | 2009155693 | 12/2009 |

OTHER PUBLICATIONS

Burpee and Latin, Reassessment of Fungicide Synergism for Control of Dollar Spot, Plant Disease, 2008, 601-606, 92(4).

Cline, OLR mating disruption just got easier, Western Farm Press, 2001, 1, 23(12).

Cockerham et al., Evaluation of Turfgrass Growth Retardant Chemicals, California Turfgrass Culture, 1971, 23-24, 21(3).

Colby, Calculating Synergistic and Antagonistic Responses of Herbicide Combinations, Weeds, 1967, 20-22, 20.

Coo-Ranger et al., Ionic Silicone Surfactants in Water-in-Silicone Oil Emulsions Containing Proteins, Polymer Preprints, 2004, 674-675, 45(1).

Cortes-Barco et al., Induced systemic rersistance against three foliar diseases of *Agrostis stolonifera* by an isoparaffin mixture, 2nd European Turfgrass Society Congress Proceedings, 2010, vol. 2.

Cortes-Barco et al., Induced systemic resistance against three foliar diseases of *Agrostis stolonifera* by (2R,3R)-butanediol or an isoparaffin mixture, Annals of Applied Biology, 2010, 179-189, 157(2).

Cortes-Barco et al., Comparison of induced resistance activated by benzothiadiazole, (2R,3R)-butanediol and an isoparaffin mixture against anthracnose of *Nicotiana benthamiana*, Plant Pathology, 2010, 643-653, 59(4).

Cranmer et al., Controlled droplet application (CDA) of fluazifop and sethoxydim for annual and perennial weed control, 1983 Meeting of the Weed Science Society of America, 1983, 23-24, Weed Abstract vol. 033 (Abs. No. 00871).

Crocker, Pesticide Screening Test for the Southern Chinch Bug, Journal of Economic Entomology, 1981, p. 730-731, 74(6).

Cropper, Towards Reducing Fungicide Use in the Control of Dollar Spot (*Sclerotinia Homoeocarpa* F.T. Bennett) Disease on Creeping Bentgrass (*Agrostis Stolonifera* L.), Master of Science Thesis, University of Kentucky, http://archive.uky.edu/handle/10225/1044 (downloaded Sep. 15, 2011).

Erhan et al., Comparisons of volatile organic chemical content of news, sheetfed, and heatset ink formulations, Journal of the American Oil Chemists' Society, 2001, 419-422, 78(4).

Findanza et al., Evaluation of fungicide and plant growth regulator tank-mix programmes on dollar spot severity of creeping bentgrass, Crop Protection, 2006, 1032-1038, 25(9).

Fidanza et al., Use of a Soil Surfactant with Fungicides for Control of Fairy Ring Disease in Turfgrass, Journal of ASTM International, 2007, 77-82, 4(4).

Furata, Strangers in a Strange Land, California Turfgrass Culture, 1971, 22-23, 21(3).

Gebhardt et al., Herbicide application with the controlled droplet applicator when using soybean oil, American Society of Agricultural Engineers Paper No. 83-1509, 1983, 12.

Gilbert et al., Spring Greenup of Dormant Non-Overseeded Bermudagrass, University of Arizona College of Agriculture2004 Turfgrass and Ornamental Research Report, http://ag.arizona.edu/pubs/crops/az1359/az13593c11.pdf (downloaded Sep. 16, 2011).

Guy et al., The performance of postemergence grass herbicides applied with sprinkler irrigation, Proceedings of the 39th annual meeting of the Southern Weed Science Society, 1986, 106, 8A.

Hartzler, Role of spray adjuvants with postemergence herbicides, ISU Weed Science Online, Mar. 7, 2001, http:/www.weeds.iastate.edu/mgmt/2001/additives.htm (downloaded Aug. 19, 2011).

Heil, Induced Systemic Resistance (ISR) Against Pathogens in the Context of Induced Plant Defences, Annals of Botany, 2002, 503-512, 89(5).

Hill, Silicone surfactants—new developments, Current Opinion in Colloid & Interface Science, 2002, 255-261, 7(5-6).

Hoffman, Analysis of Alcohol and Alkylphenol Polyethers via Packed Column Supercritical Fluid Chromatography, Ph.D. Thesis, VirginiaTech, Chapter 1.

(56) References Cited

OTHER PUBLICATIONS

Hsiang et al., Baseline sensitivity and cross-resistance to demethylation-inhibiting fungicides in Ontario isolates of *Sclerotinia homoeocarpa*, European Journal of Plant Pathology, 1997, 409-416, 103(5).
Hsiang et al., Sensitivity of *Sclerotinia homoeocarpa* to demethylation-inhibiting fungicides in Ontario, Canada, after a decade of use, Plant Pathology, 2007, 500-507, 56(3).
Jordan, Enhanced post-emergence herbicide efficacy with ultra-low volume application, Proceedings of the 48th annual meeting of the Southern Weed Science Society, 1995, 208-212, 48.
Kremer et al., Control of *Sclerotinia homoeocarpa* in Turfgrass Using Effective Microorganisms, EM World J., 2000, 16-21, 1(1).
Liu et al., Painting dormant bermudagrass putting greens, GCM, 86-91, Nov. 2007.
Lorbeer, Synergism, Antagonism, and Additive Action of Fungicides in Mixtures, Phytopathology, 1996, 1261-1262, 86(11).
McCowan, Turf Herbicide Rx: Add Oil, Agricultural Chemicals, 1968, p. 18-21, 23(4).
Nalewaja et al., Crop origin oils with grass control herbicides, Proceedings of the North Central Weed Control Conference, 1983, 3, 034 (Abstract).
Ostmeyer, The color Green, Golf Course Management, 1994, 40, 44, August.
Palla et al., Correlation of Dispersion Stability With Surfactant Concentration and Abrasive Particle Size for Chemical Mechanical Polishing (CMP) Slurries, Journal of Dispersion Science and Technology, 2000, 491-509, 21(5).
Pavlista, Paraffin enhances yield and quality of the potato cultivar Atlantic, Journal of Production Agriculture, 1995, 40-42, 8(1).
Perry, Ground Covers: Specifications and Costs, California Turfgrass Culture, 1971, 21-22, 21(3).
Puterka, Fungal pathogens for arthropod pest control in orchard systems: mycoinsecticidal approach for pear *Psylla* control, BioControl, 1999, 183-210, 44(2).
Rieke, Thatchremoval, California Turfgrass Culture, 1971, 19-20, 21(3).
Samoucha et al., Synergism in fungicide mixtures against *Pseudoperonospora Cubensis*, Phytoparasitica, 1988, 337-342, 16(4).
Schott et al., Effects of adjuvants on herbicidal action. III. Effects of petroleum and rapeseed oils on diclofop-methyl action on ryegrass, Agronomie, 1991, 27-34, 11(1).
Shaposhnikov et al., Carboxy-substituted Phthalocyanine Metal Complexes, Russian Journal of General Chemistry, 2005, 1480-1488, 75(9).
Shearman et al., Colorant Effects on Dormant Buffalograss Turf Performance, HortTechnology, 2005, 244-246, 15(2).
Trathnigg et al., Molecular Characterization of Ethoxylates by Complementary Chromatographic Techniques. Evaluation of Efficiency and Reliability, Tenside Surf. Det. 2003, 148-154, 40(3).
Tu et al., Weed Control Methods Handbook: Tools and Techniques for Use in Natural Areas, The Nature Conservancy Wildland Invasive Species Team, Apr. 2001.
Vallad et al., Systemic Acquired Resistance and Induced Systemic Resistance in Conventional Agriculture, Crop Science, 2004, 1920-1934, 44.
Van Dam et al., A Turfgrass Colorant Study, California Turfgrass Culture, 1971, 17-19, 21(3).
Vincelli, Chemical Control of Turfgrass Diseases 2010, University of Kentucky College of Agriculture, http://pest.ca.uky.edu/PSEP/Manuals/ppa1.pdf (downloaded Aug. 22, 2011).
Vol'Pin et al., Redox and fungicidal properties of phthalocyanine metal complexes as related to active oxygen, Journal of Inorganic Biochemistry, 2000, 285-292, 81(4).
Walsh et al., Biology and Management of Dollar Spot (*Sclerotinia homoeocarpa*); an Important Disease of Turfgrass, HortScience, 1999, 13-21, 34(1).
Womack et al., A vegetable oil-based invert emulsion for mycoherbicide delivery, Biological Control, 1996, 23-28, 6(1).
Yang et al., Infection of Leafy Spurge by *Alternaria alternate* and *A. angustiovoidea* in the Absence of Dew, Phytopathology, 1993, 953-958, 83(9).
Youngner, Kikuyugrass, *Pennisetum clandestinum*, and Its Control, Southern California Turfgrass Culture, 1958, 1-4, 8(1).
Youngner, Gibberellic Acid on *Zoysia* Grasses, Southern California Turfgrass Culture, 1958, 5-6, 8(1).
Youngner et al., Colorants for Dormant Bermuda and Other Subtropical Grasses, Southern California Turfgrass Culture, 1958, 7-8, 8(1).
Office Action (Restriction Requirement) for U.S. Appl. No. 11/866,157 of May 16, 2011.
International Search Report for PCT International Application No. PCT/CA2007/001762.
Written Opinion for PCT International Application No. PCT/CA2007/001762.
International Preliminary Report on Patentability for PCT International Application No. PCT/CA2007/001762.
Office Action (Restriction Requirement) for U.S. Appl. No. 10/908,538 of Feb. 26, 2009.
Office Action for U.S. Appl. No. 10/908,538 of Apr. 1, 2009.
International Search Report for PCT International Application No. PCT/CA2009/000862.
Written Opinion for PCT International Application No. PCT/CA2009/000862.
International Preliminary Report on Patentability for PCT International Application No. PCT/CA2009/000862.
Examination Report for NZ Application No. NZ590318 dated May 6, 2011.
Office Action for CA Application No. CA2,507,482 dated Jan. 18, 2011.
Office Action for CA Application No. CA2,507,482 dated Aug. 11, 2009.
Office Action (Restriction Requirement) for U.S. Appl. No. 12/492,863 dated Aug. 15, 2011.
Office Action for U.S. Appl. No. 11/866,157 dated Aug. 29, 2011.
Material Safety Data Sheet for AGRI-DEX, Helena Chemical Company, Apr. 29, 2005.
Material Safety Data Sheet for Banner MAXX, Syngenta Crop Protection, Inc., Aug. 30, 2010.
Material Safety Data Sheet for BLENDEX VHC, Helena Chemical Company, Jul. 27, 2000.
Material Safety Data Sheet for Broadcoat Spray Adjuvant, Caltex Australia Limited, Sep. 2003.
Material Safety Data Sheet for Chipco Signature, Bayer CropScience Pty Ltd, Oct. 21, 2002.
Material Safety Data Sheet for Chipco Signature, Bayer CropScience Pty Ltd, May 1, 2007.
Material Safety Data Sheet for Civitas, Petro-Canada Lubricants, Inc., Mar. 21, 2011.
Material Safety Data Sheet for Cleary 3336 Plus, Cleary Chemical Corporation, 2.1.05.
Material Safety Data Sheet for Daconil 2787, Syngenta Crop Protection Canada, Inc., Dec. 31, 2008.
Specimen Label for BLENDEX VHC, Helena Chemical Company, 2006.
Application of Fungicides for Suppression of *Fusarium* Head Blight (Scab), North Dakota State University, http://www.ag.ndsu.edu/pubs/ageng/machine/ae1148w.htm (downloaded Aug. 22, 2011).
An Integrated Approach to Insect Management in Turfgrass: Black Cutworm, Richard J. Buckley et al., Rutgers, The State University of New Jersey, http://snyderfarm.rutgers.edu/pdfs/BlackCutworms.pdf (downloaded Aug. 26, 2011).
An Integrated Approach to Insect Management in Turfgrass: Sod Webworms, Albrecht M. Koppenhofer et al., Rutgers, The State University of New Jersey, http://snyderfarm.rutgers.edu/pdfs/SodWebworms.pdf (downloaded Aug. 26, 2011).
An Integrated Approach to Insect Management in Turfgrass: White Grubs, Albrecht M. Koppenhofer et al., Rutgers, The State University of New Jersey, http://www.co.somerset.nj.us/_pdffiles/JapBeetleFS.pdf (downloaded Aug. 26, 2011).
Armyworms and cutworms in turfgrass, Erin W. Hodgson, Utah State University, http://extension.usu.edu/files/publications/factsheet/armyw-cutw-turf07.pdf (downloaded Aug. 26, 2011).

(56) References Cited

OTHER PUBLICATIONS

Bentgrass dead spot, University of Connecticut, http://www.turf.uconn.edu/pdf/research/factsheets/Disease_Bentgrass_Dead_Spot.pdf (downloaded Aug. 22, 2011).
Bentgrass Deadspot, Cornell University, http://plantclinic.cornell.edu/factsheets/bentgrassdeadspot.pdf (downloaded Aug. 22, 2011).
Biological/Biorational Products for Disease Management, University of Connecticut Integrated Pest Management, http://www.ipm.uconn.edu/ipm/greenhs/htms/biofung.htm (downloaded Aug. 22, 2011).
Biology and Control of Dollar Spot Disease, Ontario Ministry of Agriculture Food & Rural Affairs, http://www.omafra.gov.on.ca/english/crops/facts/info_turfdollarspot.htm (downloaded Aug. 22, 2011).
Black Cutworms, D.R. Smitley et al., Michigan State University Turfgrass Science, http://www.turf.msu.edu/black-cutworms (downloaded Aug. 26, 2011).
Brown Patch, Center for Turfgrass Science, Penn State College of Agricultural Sciences, http://cropsoil.psu.edu/turf/extension/factsheets/managing-diseases/brown-patch (downloaded Aug. 30, 2011).
Brown Patch, University of Guelph, http://www.uoguelph.ca/pdc/Factsheets/PDFs/127TurfBrownPatch.pdf (downloaded Aug. 30, 2011).
Brown Patch on Turfgrass, Cornell University Department of Plant Pathology and Plant-Microbe Biology, http://plantclinic.cornell.edu/factsheets/brownpatch.pdf (downloaded Aug. 30, 2011).
Chemical Control of Turfgrass Diseases 2011, University of Kentucky College of Agriculture, http://pest.ca.uky.edu/PSEP/Manuals/ppa1.pdf (downloaded Aug. 25, 2011).
Chemical Structures, The Bugwood Network, http://www.bugwood.org/PAT/22chemicalstructures.html (downloaded May 25, 2006).
Chemical Trials for Dollar Spot Disease Control Summer 2006, Guelph Turfgrass Institute 2006 Annual Research Report, http://131.104.104.3/06anrep/40-42.pdf (downloaded Aug. 22, 2011).
Clover and Other Mites of Turfgrass, W.S. Cranshaw, Colorado State University, http://www.ext.colostate.edu/pubs/insect/05505.html (downloaded Aug. 26, 2011).
Cultural practices and their effects upon turf grass growth and stress tolerance, Greenkeeper International, http://www.bigga.org.uk/about-us/magazine/back-issues/07-2006/cultural-pray-tim-butler/00919.html (downloaded Aug. 24, 2011).
Dead Spot Disease of Creeping Bentgrass, University of Maryland, http://www.hgic.umd.edu/content/documents/TT-14DeadSpot.pdf (downloaded Aug. 22, 2011).
Dead Spot of Creeping Bentgrass and Hybrid Bermudagrass, Plant Management Network, http://www.plantmanagementnetwork.org/pub/ats/diagnostic/2005/deadspot/ (downloaded Aug. 22, 2011).
Dollar Spot on Turfgrass, Cornell University, http://counties.cce.cornell.edu/wyoming/agriculture/resources/ipd/dollar_spot_turfgrass.htm (downloaded Aug. 22, 2011).
EPA: Pesticides—Inert (other) Pesticide Ingredients in Pesticide Products, U.S. Environment Protection Agency, http://www.epa.gov/opprd001/inerts/lists.html (downloaded Sep. 11, 2007).
Fungicide Resistance Action Committee Code List: Fungicides sorted by mode of Action, Fungicide Resistance Action Committee, http://www.frac.info/frac/publication/anhang/FRAC%20Code%20List%202011-final.pdf (downloaded Aug. 22, 2011).
Fungicide Synergy, Kansas State University, http://www.ksuturf.conn/LISTServArchive/2009_02_26_Fungicide_Synergy.pdf (downloaded Aug. 22, 2011).
Propiconazole Pesticide Information Profile, Extension Toxicology Network, http://pmep.cce.cornell.edu/profiles/extoxnet/metiram-propoxur/propiconazole-ext.html (downloaded Aug. 19, 2011).
Rhizoctonia Large Patch Disease of Zoysiagrass and Bermudagrass, University of Arkansas Division of Agriculture, http://www.uaex.edu/Other_Areas/publications/PDF/fsa-7527.pdf (downloaded Aug. 30, 2011).
Silicone Surface-Active Agents, Donna Perry, Dow Corning Corporation, http://www.dowcorning.com/content/publishedlit/26/1365.pdf (downloaded Aug. 30, 2011).
Turf Tip, University of Arkansas, http://turf.uark.edu/turfhelp/archives/030509.html (downloaded Aug. 22, 2011).
Turfgrass Diseases: Leaf Spots and Tip Blights, Melting Out, Crown and Root Rots, University of Rhode Island Landscae Horticulture Program, http://www.uri.edu/ce/factsheets/sheets/leafspotsetc.html (downloaded Aug. 30, 2011).
Turfgrass Disease Profiles Brown Patch, Purdue University, http://www.ces.purdue.edu/extmedia/BP/BP-106-W.pdf (downloaded Aug. 30, 2011).
Turfgrass Disease Profiles Dollar Spot, Purdue University, http://www.ces.purdue.edu/extmedia/BP/BP-105-W.pdf (downloaded Aug. 22, 2011).
Turfgrass Disease Profiles Leaf Spot/Melting Out, Purdue University, http://www.ces.purdue.edu/extmedia/bp/bp-103-w.pdf (downloaded Aug. 30, 2011).
Turfgrass Disease Profiles Gray Leaf Spot, Purdue University, http://www.ces.purdue.edu/extmedia/BP/BP-107-W.pdf (downloaded Aug. 23, 2011).
Turfgrass Disease Profiles Gray Snow Mold, Purdue University, http://www.ces.purdue.edu/extmedia/BP/BP-101-W.pdf (downloaded Sep. 15, 2011).
Turfgrass Disease Profiles Rhizoctonia Large Patch, Purdue University, http://www.extension.purdue.edu/extmedia/BP/BP-117-W.pdf (downloaded Aug. 30, 2011).
Turfgrass Disease Profiles Pink Snow Mold and Microdochium Patch, Purdue University, http://www.ces.purdue.edu/extmedia/BP/BP-102-W.pdf (downloaded Sep. 15, 2011).
Turfgrass Insects Sheet 1, D.E. Short et al., University of Florida, http://edis.ifas.ufl.edu/in025 (downloaded Aug. 26, 2011).
Turfgrass Insects Sheet 2, D.E. Short et al., University of Florida, http://edis.ifas.ufl.edutin026 (downloaded Aug. 26, 2011).
Turfgrass Pest Control, West Virginia University, http://www.wvu.edu/~exten/infores/pubs/pest/pcertil9.pdf (downloaded Aug. 22, 2011).
Understanding Bentgrass Dead Spot, USGA Turfgrass and Environmental Research Online, http://turf.lib.msu.edu/tero/v02/n02.pdf (downloaded Aug. 22, 2011).
Material Data Safety Sheet for JMS Stylet-Oil (Mar. 1, 1994).
Agnello, Arthur M., "Petroleum-derived spray oils: chemistry, history, refining and formulation", in Beattie, G. A. C., Watson, D. M., Stevens, M., Spooner-Hart, R. and Rae, D. J. (eds). Spray Oils Beyond 2000—Sustainable Pest & Disease Management. University of Western Sydney (2002).
"It pays to be pure", http:/www.findarticles.com/p/articles/mi_qa3824/12_200405/ai_n9424665/print, Meister Media Worldwide (May 2004).
"The Stylet-Oil User's Guide", http:/www.stylet-oil.com/ (Mar. 22, 2005).
"Horticultural Oils", http:/www.ipmofalaska.com/filed/hortoils.html, IPM of Alaska (downloaded Apr. 5, 2005).
PureSpray Spray Oil 10E, Delaware Department of agriculture Pesticide Database Searches (downloaded from DDA website Apr. 7, 2005).
Pesticide Product Label System (PPLS)—Search Results for PureSpray Oil 10E—Approval dates Apr. 21, 2000, Jul. 23, 2002, Sep. 24, 2003, Mar. 5, 2004 (downloaded from EPA Office of Pesticide Programs website Apr. 27, 2005.
"An Online Guide to Plant Disease Control", Oregon State University Extension http:/plant-disease.orst.edu/ (downloaded May 16, 2005) (online version of the "2005 Pacific Northwest Plant Disease Management Handbook", Oregon State University Extension).
Material Safety Data Sheet for Daconil Ultrex, Syngenta Crop Protection Canada, Inc., Aug. 1, 2009.
Material Safety Data Sheet for FORE 80 WP Rainshield, Dow AgroSciences, Jun. 1, 2001.
Material Safety Data Sheet for FORE Fungicide, Rohm and Haas Company, Oct. 16, 1995.
Material Safety Data Sheet for Harmonizer, Petro-Canada Lubricants Inc., May 6, 2011.

(56) References Cited

OTHER PUBLICATIONS

Material Safety Data Sheet for Lambent MFF-199 SW, Lambent Technologies Corp., Jan. 31, 2005.
Material Safety Data Sheet for Lambent MFF 159-100, Lambent Technologies Corp., Apr. 4, 2006.
Material Safety Data Sheet of PEPTOIL, Drexel Chemical Company, Jan. 7, 2005.
Material Safety Data Sheet for Silsurf A008-UP, Siltech Corporation, Aug. 21, 2009.
Material Safety Data Sheet for Sylgard 309 Silicone Surfactant, Dow Corning Corporation, Apr. 5, 2001.
Material Safety Data Sheet for SURF AC 820, Drexel Chemical Company, Jul. 22, 2005.
Specimen Label for Fore 80WP Rainshield, Dow AgroSciences, May 17, 2004.
Specimen Label for AGRI-DEX, Helena Chemical Company, 2005.
Label for Banner MAXX, Syngenta Crop Protection, Inc., May 2004.
Specimen Label for BLENDEX VHC, Helena Chemical Company, May 2006.
Specimen Label for Civitas, Petro-Canada Lubricants, Inc., May 2004.
Specimen Label for Cleary 3336 Plus, Cleary Chemical Corporation, May 2004.
Specimen Label for Harmonizer, Petro-Canada Lubricants, Inc., May 2004.
Specimen Label for Peptoil, Drexel Chemical Company, May 2004.
Label for Rovral Green GT, Bayer CropScienc Inc., May 2004.
Specimen Label for Sil-Fact, Drexel Chemical Company, May 2004.
Specimen Label for Sil-MES 100, Drexel Chemical Company, May 2004.
Specimen Label for Surf-Ac 820, Drexel Chemical Company, May 2004.
Specimen Label for Chipco Signature, Bayer CropScience Pty Ltd, May 2004.
2006 Pest Control Recommendations for Lawn and Turf Areas, Rutgers Cook College, http://njaes.rutgers.edu/pubs/publication.asp?pid=e037 (downloaded Aug. 25, 2011).
Product Bulletin for Caltex, Caltex Australia, http://www.caltex.com.au/products_oil_detail_print.asp?id=229 (downloaded Aug. 2, 2006).
Leaflet for Volpo, Croda Chemicals Europe Ltd, http://www.chservice.ru/download/DC%20Volpo.pdf, May 2004.
Pamphlet for Daconil 2787, Syngenta Crop Protection Canada, Inc., http://www.mountainviewturf.com/our-products/pdf/chemical-labels/Daconil.pdf, May 2004.
Pamphlet for Daconil Ultrex, Syngenta Crop Protection Canada, Inc., http://www.syngentacropprotection-us.com/pdf/labels/DACONIL_Ultrex_28354_en_pamphlet.pdf, May 2004.
Brochure for Civitas, Petro-Canada, http://www.civitasturf.com/pdf/CIVITAS-technical-brochure.pdf (downloaded Aug. 22, 2011).
Technical Bulletin for Civitas, Petro-Canada, http://www.civitasturf.com/pdf/techBulletin.pdf (downloaded Aug. 22, 2011).
Technical Data Sheet for Lambent MFF-199 SW, Lambent Technologies Corp., May 2004.
Technical Data Sheet for Lambent MFF 159-100, Lambent Technologies Corp., May 2004.
Technical Information for Lutensol AT types, BASF SE, May 2004.
Product Information Sheet for Silgard 309 Silicone Surfactant, Dow Corning Corporation, May 2004.
Technical Data Sheet for Silsurf A008-UP, Siltech Corporation, May 2004.
A Guide to Major Turfgrass Pests & Turfgrasses, NC State University, http://www.turffiles.ncsu.edu/PDFFiles/004041/ag348.pdf (downloaded Aug. 25, 2011).
Gray leaf spot of perennial ryegrass, Kansas State University Turfgrass Research, (downloaded Aug. 23, 2011).
Gray Leaf Spot of Perennial Ryegrass, Plant Management Network, http://www.plantmanagementnetwork.org/pub/php/diagnosticguide/2003/ryegrass/ (downloaded Aug. 23, 2011).
Herbicide List for Identification of Unknown Herbicides, Northeastern Collegiate Weed Science Contest, http://www.newss.org/docs/mop/addendum-9.pdf, May 2004.
Herbicide Recommendations for Turfgrass: Postemergence Broadleaf Herbicides, Ontario Ministry of Agriculture, Food and Rural Affairs, http://www.omafra.gov.on.ca/english/crops/pub75/17turpbh.htm (downloaded Sep. 10, 2001).
Herbicide—Wikipedia, the free encyclopedia, http://en.wikipedia.org/wiki/Herbicide (downloaded Aug. 29, 2006).
Insect Pest Management on Golf Courses, Eileen A. Buss, University of Florida, http://edis.ifas.ufl.edu/in410 (downloaded Aug. 26, 2011).
Insect Pest Management on Turfgrass, Eileen A. Buss, University of Florida, http://edis.ifas.ufl.edu/ig001 (downloaded Aug. 26, 2011).
Integrated Pest Management—Identification & Management of Turfgrass Disease, University of Missouri, http://extension.missouri.edu/p/IPM1029 (downloaded Aug. 25, 2011).
Leaf Spot and Melting-out (crown and root rot) Diseases—Center for Turfgrass Science, Penn State College of Agricultural Sciences, http://cropsoil.psu.edu/turf/extension/factsheets/managing-diseases/leaf-spot (downloaded Aug. 30, 2011).
Performance of generic phosphite fungicides: A status report, AgNet Mar. 8, 2004, The Canadian Phytopathological Society, http://www.cps-scp.ca/pathologynews/performanceofgenericfungicides.html (downloaded Aug. 22, 2011).
Pest Control for Professional Turfgrass Managers 2011, North Carolina State University, http://www.turffiles.ncsu.edu/PDFFiles/004176/AG408PestControl_Professionals.pdf (downloaded Sep. 15, 2011).
Propiconazole Pesticide Information Profile, Extension Toxicology Network, http://pmep.cce.cornell.edu/profiles/extoxnet/metirann-propoxur/propiconazole-ext.html (downloaded Aug. 19, 2011).

* cited by examiner

SPRAY OIL AND METHOD OF USE THEREOF FOR CONTROLLING TURFGRASS PESTS

CROSS REFERENCE TO RELATED APPLICATIONS

This application is a divisional application of pending U.S. patent application Ser. No. 10/908,538 filed on May 16, 2005, claiming priority of U.S. Patent application Ser. No. 60/572,544, filed May 18, 2004 and Canadian Application 2,472,806 filed Jun. 30, 2004; the entirety of which are incorporated herein by reference.

FIELD OF THE INVENTION

The invention relates to spray oils, and in particular to paraffinic spray oils and their method of use for controlling turfgrass pests such as harmful insects and fungi.

BACKGROUND OF THE INVENTION

In the field of agriculture and horticulture, it is well known to use spray oils in the control plant pests such as harmful insects, fungi, and microorganisms such as bacteria and viruses. The base for such spray oils are generally made of naturally occurring oils such as refined petroleum products, e.g., paraffinic oils, or oils extracted from plants, vegetables or animals.

Spray oils are often formulated as an oil-in-water (O/W) emulsion which is periodically applied directly to plants. An emulsion is a dispersed system containing at least two normally immiscible phases, one being dispersed as droplets in the other. Emulsions are thermodynamically unstable due to excess free energy associated with the surface of the dispersed droplets such that the particles tend to flocculate (clumping together of dispersed droplets or particles) and subsequently coalesce (fusing together of agglomerates into a larger drop or droplets) to decrease the surface energy. If these droplets fuse, the emulsion will "break", i.e. the phases will separate, destroying the emulsion and making it difficult to prepare formulations that have a suitable shelf-life for storage. To prevent or slow breaking of an emulsion, an emulsifying agent is typically added. The type and concentration of a particular emulsifying agent will depend, inter alia, on the emulsion phase components and the desired result.

Spray oils are often used as a carrier for traditional synthetic chemical pesticides and for enhancing the activity of such pesticides. Alternatively, certain spray oils can be used alone as a bona fide pest control agent, in which case the oil component itself is the active ingredient. Spray oil alone is thought to act by coating the pests to induce a potential variety of effects, including suffocation of insects, modification of insect feeding and egg laying behavior, destruction of fungi cell walls, removal of humidity and interference with physical interactions of fungi or viruses with the host plant.

For a number of reasons, it is preferable to use spray oils without added chemical pesticides. For example, as compared with chemical pesticides, spray oils are generally considered to be safer for humans, are less harmful to beneficial insects such as bees, and are more quickly degraded. In addition, the cost of effort of manufacturing chemical pesticides is avoided, while spray oils can be simply made out of inexpensive fractions of petroleum oil. The main limitation of spray oils is their potential to cause plant injury (phytotoxicity) in some situations, as with certain sensitive plants or plants under drought stress.

The use of spray oil alone has been especially useful in effectively controlling a variety of pests in tree crops, such as apple and orange trees, grapes, vegetables, and flowering and ornamental plants. Examples of such commercially available spray oils include Stylet-Oil (JMS Flower Farms Inc., Vero Beach, Calif.) and PureSpray 10E (Petro-Canada, Calgary, Alberta), both of which contain paraffin oil, also known as mineral oil, as the active ingredient.

A particularly desirous use of spray oil alone is in the control of turfgrass pests. Turfgrass generally includes any maintained grass surface, such as lawns and golf courses. Turfgrass has been traditionally treated with synthetic chemical compounds to control pests, resulting is high maintenance costs and harmful effects to humans and the environment.

Although several non-petroleum spray oils have been disclosed as having use in treating turfgrass, such spray oils have not found widespread commercial use. For example, US patent application publication no. 2003/0198686 to Keen discloses the use of a spray oil composed of a combination of fish oil and plant oil to control turfgrass pests. However, fish oils tend to be phytotoxic due to alcohol and acid products formed by ester hydrolysis and have an unpleasant smell. US patent application publication no. 2003/0194454 to Bessette discloses the use of rosemary oil and wintergreen oil, alone or in combination, in controlling turfgrass pests; however, such non-petroleum oils tend to become rancid upon prolonged exposure to sunlight.

To Applicant's knowledge, there is no petroleum-based spray oil indicated for use on turfgrass. Although Stylet-Oil, provided as a concentrate of 97.1% v/v paraffin oil and 2.9% v/v non-ionic emulsifier, is indicated for use against stripe rust disease on grass grown for seed when applied at an oil dosage of 0.2-0.4 gal/acre, it is well established that turfgrass differs significantly from grass grown for seed in several respects. For example, the major diseases that affect grass grown for seed and turfgrass are not coterminous. In particular, as outlined in the Online Guide to Plant Disease Control of Oregon State University Extension (http://plant-disease.ippc.orst.edu/) and in the hardcopy version, "The 2004 PNW Plant Disease Management Handbook", the diseases of prime concern in the production of grass grown for seed include Rusts, Smuts, Molds, Silvertop, Barley Yellow Dwarf, Blind Seed, Ergot, Powdery Mildew, while the diseases of prime concern in turf management include Anthracnose, Dollar Spot, Brown Patch, Grey Snow Mold and Pink Snow Mold. Further, for the few diseases that are in common, the chemical treatment regimes can be different. For example, although Powdery Mildew is not a major problem in turfgrass, when necessary, treatment with azoxystrobine fungicide is recommended at a dosage of 4.1-8.7 oz of solid azostrobine per acre, compared with 1.65-4.05 oz of solid azoxysrtobine per acre for grass grown for seed. The differences between grass grown for seed and turfgrass may be due to physiological and physical differences imposed by different growing conditions and environments, the greater degree of stress imposed on turfgrass due to injuries caused by traffic and repeated mowing of turfgrass, and the removal of pest control agents when the turfgrass in mowed.

In view of the foregoing, there is a need in the art for an improved spray oil composition for control of pests of turfgrass.

SUMMARY OF THE INVENTION

The invention provides a paraffinic spray oil composition that is applied to turfgrass as an oil-in-water (O/W) emulsion and is effective in controlling turfgrass pests without added synthetic chemical pesticides.

In one aspect of the invention, the spray oil contains a quick break emulsifier in a proportion with a paraffinic oil that allows the oil to be quickly released from the O/W emulsion upon application to the turfgrass for contact of pests thereon. In one embodiment, the spray oil contains an oil-to-emulsifier ratio ranging from 95:5 to 99.95:0.05, preferably from 98.5:1.5 to 99.9:0.1, and most preferably 99.2:0.8. The spray oil can be provided in a variety of formulations, including an oil-emulsifier concentrate and O/W emulsions. The O/W emulsion generally comprises paraffinic oil at about 1-50% by weight, and preferably about 10-30% by weight.

The paraffinic oil includes any oil enriched in paraffin. In one embodiment, the paraffin has a number of carbon atoms ranging from about 12 to about 50 (C12 to C50) or combinations thereof, and preferably with a carbon number ranging from about C16 to about C35 and with an average carbon number of about C23. Preferably, the paraffin content of the paraffinic oil is at least about 80%, and more preferably at least about 90%, and most preferably at least about 99%. Suitable paraffinic oils have been refined to remove impurities that are harmful to plants, especially aromatics.

The emulsifier can be any quick break emulsifier suitable for achieving the desired result. Exemplary emulsifiers include alkyl phenol ethoxylates, nonylphenolethyoxylate, dodecylphenolethoxylates, and ethoxylated alcohol/glycerol oleate mixtures, or combinations thereof.

Notably, it is generally considered that turfgrass is under stress due to its use and maintenance, such that there is an expectation that turfgrass is particularly susceptible to potential toxic effects of spray oils. Surprisingly, Applicant has found that when the spray oil is applied to turfgrass, particularly at an oil dosage that is higher than typically used in other spray oil applications, the spray oil is effective in controlling a variety of turfgrass pests, including insects and fungi, with little or no phytotoxic effects.

Accordingly, in another aspect of the invention, the invention provides a method for controlling turfgrass pests comprising applying an effective amount of the spray oil to the turfgrass. In one embodiment, the effective amount provides a paraffinic oil dosage of at least about 0.5 gal/acre, preferably from about 5 gal/acre to about 60 gal/acre, and more preferably from about 10 gal/acre to about 20 gal/acre, and which can be applied periodically as needed. The optimal dosage may vary according to the type of turfgrass, the type and amount of pest on the turfgrass, and the environmental conditions, and can be readily determined by established biological tests.

Unexpectedly, Applicant has also found that when the spray oil is applied to turfgrass as indicated for controlling pests, the growth of the turfgrass is enhanced.

Accordingly, in another broad aspect of the invention, the invention provides a spray oil and method of use of the spray oil for enhancing the growth of turfgrass comprising applying an effective amount of the spray oil to the turfgrass.

In addition, the components of the invention are provided as kits for use in controlling turfgrass pests and for enhancing the growth of turfgrass, wherein the kits comprise the spray oil and instructions for use of the spray oil.

DESCRIPTION OF THE PREFERRED EMBODIMENT

The spray oil composition of the present invention generally comprises a paraffinic oil as the active ingredient and a quick break emulsifier. The composition is normally provided as an emulsifiable concentrate containing the paraffinic oil and emulsifier, which is thereafter prepared for use as a diluted oil-in-water (O/W) emulsion. In the O/W emulsion, the oil phase is dispersed in the continuous aqueous phase via the emulsifier. As described in more detail below, the ratio of oil to emulsifier allows the O/W emulsion to quickly break upon application to the turfgrass, thereby releasing the oil component onto the grass blade for the control of pests thereon. Surprisingly, when used at concentrations effective for controlling turfgrass pests, there are little or no phytotoxic effects. Furthermore, it was unexpectedly observed that turfgrass treated with the spray oil exhibited more vigorous growth than that observed for untreated turfgrass and turfgrass treated with chemical pest control agents.

As used herein, the terms "turfgrass" or "grass" generally refer to grasses that are periodically cut or mowed to provide a groundcover for various utility, recreational or aesthetic purposes. Exemplary turfgrasses include Fescues, Rye, Bent, Bahia, St. Augustine, Centipede, Kentucky bluegrass, Zoysia Native Grasses (e.g., Buffalo grass, Blue Grama and Wheatgrasses), Seashore *Paspalum*, Carpet Grass, Buffo, and Beach Grass. Such grasses are typically found locations such as parks, golf courses, sports fields, sod farms, roadsides, and lawns for housing residences, commercial sites, and institutional grounds.

As used herein, the terms "turfgrass pest" or "pest" generally refer to living organisms occurring on turfgrass that are not desired to occur on turfgrass or that cause damage to turfgrass. Turfgrass pests include but are not limited to insects (adult and larval forms), fungi, and microorganisms such as bacteria and viruses, and are particularly contemplated to include stationary fungus, creeping, crawling hopping or flying insects, or burrowing or subterranean pests that reside on the grass blade during a pre-adult stage of their lifecycle. Exemplary turfgrass pests include, for example, bluegrass weevils, cutworms, sod webworms, pillbugs, grubs, aphids, mites, chinch bugs, chafers, beetles, grasshoppers, scales, cranefly, earwigs, slugs, ants, fleas, mealybugs, ticks, and causative agents of Grey Leaf Spot, Dollar Spot, Grey Snow Mold, Pink Snow Mold, Brown Patch, Anthracnose, Yellow Turf, Powdery Mildew, *Pythium* Foliar Blight Disease, Necrotic Ring Spot, Pink Patch, Red Thread, Leaf Blight, Yellow Patch, Downey Mildew, *Pythium* Blight, Rusts, Stripe Smut, Summer Leaf Spot, Take-All Patch, and *Microdochium* Patch Disease, or combinations thereof.

As used herein, the term "control" or "controlling" generally refer to preventing, destroying, repelling, or mitigating turfgrass pests.

As used herein, the term "spray oil" generally refers to a paraffinic oil-containing composition, including concentrates and oil-in-water emulsion formulations.

Generally defined, paraffinic oil is any oil enriched in paraffin (saturated hydrocarbon). Particularly useful paraffinic oils of the present invention include paraffins having a number of carbon atoms ranging from about 12 to about 50 (C12 to C50) or combinations thereof, and preferably with a carbon number ranging from about C16 to about C35 and with an average carbon number of about C23. Preferably, the paraffinic oil has a paraffin content of at least about 80%, with a paraffin content of at least about 90% being more preferred, and a paraffin content of at least about 99% being most preferred. Suitable paraffin oils include HT100 and High Flash Jet, both manufactured by Petro-Canada, Calgary, Alberta.

Preferably, the paraffinic oil is refined so as to substantially remove impurities in the oil that are associated with plant injury, such as aromatic compounds, compounds containing sulfur, nitrogen or oxygen. For example, the paraffin oil preferably contains an aromatic content of less than 10% w/w and more preferably, less than 2% w/w.

In general, the emulsifiers of the present invention are of the so-called "quick break" variety such that, when present in a suitable proportion or ratio with the oil, the resulting quick break O/W emulsion quickly releases the oil phase (active ingredient) upon application to the turfgrass. Consequently, there is less runoff of the O/W emulsion from the grass blades as compared to more stable O/W emulsions, such that a sufficient amount of oil adheres to the turfgrass for a sufficient amount of time to effectively contact and control associated turfgrass pests. Preferably the oil resides on the turfgrass for a period of not less than one hour.

Emulsifiers that are particularly suited for use in the spray oil include but are not limited to alkyl phenol ethoxylates, nonylphenolethyoxylate, dodecylphenolethoxylates, and ethoxylated alcohol/glycerol oleate mixtures, or combinations thereof. Emulsifiers that have minimal environmental risk, such as ethoxylated alcohol/glycerol oleate mixtures, are preferred.

The paraffin oil and emulsifier are present in a weight ratio of oil:emulsifier ranging from about 95:5 to 99.95:0.05, preferably from about 98.5:1.5 to 99.9:0.1, and more preferably about 99.2:0.8. Applicant has found that such ratios are desirable for optimum performance of the spray oil on turfgrass, while at the same time providing suitable stability of the O/W emulsion to allow for a reasonable timeframe for its preparation and storage.

The spray oil is normally provided as an oil-emulsifier concentrate containing about 95-99.95% by weight paraffinic oil and 0.0.05-5.0% by weight (w/w) emulsifier, preferably about 98.5-99.9% by weight paraffinic oil and 0.1-1.5% by weight emulsifier, and more preferably about 99.2% by weight paraffinic oil and about 0.8% by weight emulsifier. The concentrate can be prepared as described in Example 1 below, or by any suitable method as is known in the art so as to provide a uniform solution of paraffinic oil and emulsifier.

The spray oil can also be provided as a kit which includes the spray oil and instructions for using the spray oil in packaged form. Preferably the paraffinic oil and emulsifier are provided as a pre-mixed concentrate, however, the paraffinic oil and emulsifier may also be provided as individual components.

For use, the paraffinic oil-emulsifier concentrate is admixed with water to form an O/W emulsion. In particular, the concentrate is diluted in water to provide a final paraffinic oil content of ranging from about 1% to 50% by weight, and preferably from of about 10% to 30% by weight. If a concentrate is not used, the individual components can simply be admixed simultaneously at their desired final amounts. Alternatively, emulsifiers provided as aqueous solutions can be premixed with water prior to admixing with the paraffinic oil.

Any suitable method for forming an O/W emulsion can be used, as is known in the art, such as that described in Example 1 below. Such methods usually involve tank mixing of the components by applying shear using a paddle mixer or blender. Alternatively, the separate components can be combined at the nozzle of a spray gun to form the O/W emulsion. In any case, the O/W emulsion should be prepared with one or two hours before use.

Preferably, the water component is distilled water or other such water having low mineral electrolyte content. Mineral electrolytes may cause the O/W emulsion to break prematurely, such as during storage or before the O/W emulsion has spread evenly over the grass blade, and are therefore not desirable.

The formulations can also include compatible customary additives or adjuvants for turfgrass protection. These include, for example, surfactants, dispersants, wetters, thickeners, organic solvents, cosolvents, antifoams, carboxylic acids, preservatives, stabilizers, and the like. Although not required, chemical pesticides and herbicides can also be included in the emulsions.

To control turfgrass pests, the O/W emulsion is applied to the turfgrass to provide an oil dosage that is sufficient to effectively control turfgrass pests. The spray oil may also be reapplied as required. Exemplary application regimens are provided in Table 1.

TABLE 1

Exemplary spray oil regimens

| % oil by weight of O/W emulsion | spray volume of O/W emulsion | dosage of oil (active ingredient) |
|---|---|---|
| 1-50% | 10-100 gal/acre | 0.1-50 gal/acre |
| 10-30% | 50-200 gal/acre | 0.5-60 gal/acre |

In general, the preferred paraffinic oil dosage is at least about 0.5 gal/acre, preferably ranging from about 0.5 gal/acre to about 60 gal/acre, and more preferably ranging from about 10 gal/acre to about 20 gal/acre. However, the most effective treatment for a specific application will generally depend on the type of turfgrass, the type of pest(s), the level of infestation and the environmental conditions and may be readily determined by established biological tests known to those skilled in the art. For example, Applicant has found that the optimal oil dosage for controlling Snow Mold is about 20 gal/acre to about—30 gal/acre.

The spray oil can be applied to turfgrass by spraying, misting, sprinkling, pouring, or any other suitable method for achieving the desired result. Preferably, the O/W emulsion is applied by spray methods, for example, using a standard spray apparatus, in which case the droplet size, pressure and volume delivered may be suitably adjusted for a particular application.

When used as described herein, the O/W emulsion of the present invention is effective in controlling a variety of turfgrass pests. Optimal control is achieved by adjusting the timing of the application and dosage so as to target the turfgrass pest when it is most vulnerable, such as during egg or crawler stages.

Importantly, despite the application of high dosages of the spray oil to turfgrass, the spray oil has little or no perceptible phytotoxic effect. Furthermore, Applicant has observed that the treated turfgrass has a pleasant residual luster and, with the exception of spray oil with a high C40 or greater carbon content, the grass is not greasy or oily to the touch. As an unexpected benefit, the treated turfgrass appeared to exhibit more vigorous growth than untreated turfgrass or turfgrass treated with chemical pest control agents alone (i.e. no oil applied).

The following examples are provided to better illustrate various embodiments of the invention and are not intended to limit the scope of the invention.

Example 1

General Materials and Methods

Oils and Emulsifiers

The following oils and emulsifiers shown in Tables 2 and 3 were used as indicated in the examples.

TABLE 2

Oils

| Oil | Source | Type | No. Carbons | Ave. |
|---|---|---|---|---|
| HT100 | Petro-Canada* | >99% paraffin oil fraction | C16 to C40 | C27 |
| High Flash Jet | Petro-Canada* | >99% paraffin oil fraction | C12 to C21 | C16 |
| LSRD | Petro-Canada* | >99% paraffin oil fraction | C12 to C21 | C16 |

*Calgary, AB, Canada

TABLE 3

Emulsifiers

| Emulsifier | Source | Components |
|---|---|---|
| AL3149 | Uniqema* | C10 to C16 alcohol ethoxylates and glycerol oleate |
| AL3313 | Uniqema* | Polyoxyethyene lauryl ether, C10 to C16 alcohol ethoxylates, and glycerol oleate |

*New Castle, DE, USA

Preparation of Concentrates

Concentrate formulas as described in the following examples were prepared by adding the emulsifier to the oil at the indicated amounts under mild agitation at room temperature or with mild heating at about 50° C.

Concentrate Formulations

The following concentrate formulations shown in Table 4 were used as indicated in the examples.

TABLE 4

Concentrate formulations (all values in % w/w of concentrate)

| | Oil | Emulsifier | Examples |
|---|---|---|---|
| P1 | 99.5% HT100 | 0.5% AL3313 | 3 |
| P2 | 50% HT100 + 49.5% High Flash Jet | 0.5% AL3313 | 3, 4 |
| P3 | 95% HT100 | 5% AL3313 | 3 |
| P4 | 99.5% HT100 | 0.5% AL3149 | 5 |
| XPO2 | 99.5% of 50/50 blend of LSRD + HT100 | 0.5% AL3313 | 6 |
| PC1 | 99.25% HT100 | 0.75% AL3149 | 7, 8, 9 |
| PC2 | 99.25% of 50/50 blend of LSRD + HT100 | 0.75% AL3313 | 8 |

Preparation of Oil-in-Water Emulsions

Oil-in-water (O/W) emulsions as described in the following examples were prepared by mixing the concentrate with water as indicated using a paddle mixer under low shear conditions for a period of several minutes or until the solution becomes transparent. The O/W emulsions were typically prepared in advance and stored for later use.

Example 2

Testing for Proper Adhesion of Oil on Turfgrass

To determine the impact of the oil to emulsifier ratio on proper adhesion of the oil on turfgrass, an oil-soluble blue dye, Agent 376, was added to O/W emulsions at 0.2% by weight during admixing. The O/W emulsions were prepared from concentrates having various ratios of HT100 to AL3149 (see Tables 2 and 3 for compositions of HT100 and Al3149, respectively), and with an oil content of 10% by weight of the O/W emulsion. Individual blades of Vertical Palm Grass were hung vertically and 100 ml of the dyed-O/W emulsion was applied to a set of 5 blades. The relative staining of turfgrass was determined by visual observation, with a higher degree of staining being indicative of better adhesion. The results, as shown in Table 5, indicate that the ratio of oil to emulsifier needs to be adjusted to achieve optimal adhesion of the oil on the turfgrass.

TABLE 5

Staining of turfgrass

| ratio of oil:emulsifier | Staining |
|---|---|
| 98.8:1.2 | Light |
| 99.4:0.6 | Dark |
| 99.5:0.5 | Darkest |
| 99.94:0.06 | Darkest |
| 99.95:0.05 | Darkest |

Example 3

Control of Oriental Beetle Grubs

The effect of different O/W emulsion formulations when applied at different dosages to turfgrass were evaluated for their effectiveness in controlling oriental beetles in Perennial ryegrass. Oriental beetle grubs were collected in the fall and over-wintered. The following spring, turfgrass grown in small containers was inoculated with the grubs at a density of 5 grubs/pot prior to application of O/W emulsion to the turfgrass. P1, P2 and P3 concentrates (see Table 4) were prepared as O/W emulsions and applied to the turfgrass using a spray volume equivalent to 88 gal/acre (2 gal/1000 sq ft) to provide the oil dosages shown in Table 6.

TABLE 6

Dosage of emulsions

| | % oil in O/W emulsion | kg oil/hectare | lb oil/acre | gal oil/acre |
|---|---|---|---|---|
| Low | 6.3 | 43 | 39 | 5.5 |
| Medium | 12.3 | 87 | 77 | 10.8 |
| High | 49.1 | 346 | 309 | 43.2 |

After 14 days, the grubs were counted to determine their mortality compared to untreated turfgrass. The results as averaged from 7 trials, as shown in Table 7, demonstrate that the spray oil is useful in controlling insect pests in turfgrass.

TABLE 7

Control of oriental beetle grubs in perennial ryegrass

| | % increase in mortality |
|---|---|
| P1 low | 143 |
| P1 med | 86 |

TABLE 7-continued

Control of oriental beetle grubs in perennial ryegrass

| | % increase in mortality |
|---|---|
| P1 high | 115 |
| P2 low | 43 |
| P2 low | 157 |
| P2 med | 71 |
| P3 high | 43 |

Example 4

Control of Chinch Bugs

To determine the efficacy of the invention in controlling Southern chinch bugs (*Blissus insularis*) under field conditions, a cylinder method for field pesticide screening reported by Crocker and Tubbs (1981, J. Econ. Entomol. 74: 730-731) was used. In April, polyvinyl chloride (PVC) cylinders were set into holes dug in plots of St. Augustine grass, with 5 cylinders as replicates in each of 5 plots (25 cylinders total). Each cylinder was 6 inches in diameter (~1.5 sq. ft.) by 6 inches high and driven into the soil so that the rim was about 4 inches above the soil surface. Southern chinch bugs were field collected from Palm Beach County, Fla. and 40 chinch bugs (adults and medium to large size nymphs) were put into each of the 25 cylinders. Each cylinder was then covered with fine mesh cloth held in place with rubber bands to allow air, sunlight, and rain into the cylinders. The next day, the cloth tops were removed from some of the cylinders and a 10% O/W emulsion prepared from P2 concentrate (see Table 4) was applied at a dosage corresponding to 17.4 gal oil/acre to the cylinders using a $CO_2$ backpack sprayer at 40 psi. The cloth tops were thereafter quickly replaced. The other cylinders were used as untreated controls. After 7 days, the 25 cylinders were dug up and each cylinder was placed in a separate bucket. The buckets were slowly flooded with water in a laboratory and live chinch bugs surfacing were counted.

The untreated control cylinders had a mortality of 0%, while the treated cylinders had an average mortality of 39%, thereby demonstrating that the spray oil is useful in controlling insect pests in turfgrass.

Example 5

Control of Grey Leaf Spot

Gray Leaf Spot is a turfgrass disease caused by the fungus *Cersospora zeas-maydis*. Initial symptoms of Grey Leaf Spot include tiny, brown spots or lesions on leaves and stolons, which quickly enlarge and become oval or elongated in shape. Mature lesions have a gray necrotic center with a brown to red boarder within a chlorotic periphery. Severe infection results in a scorched appearance and the turf density becomes reduced.

Experiments to determine the effect of the spray oil on Grey Leaf Spot in St. Augustine turfgrass were conducted in Florida from May through to mid-August. A 30% O/W emulsion was prepared from P4 concentrate (see Table 4) and the emulsion was applied biweekly to the turfgrass at a spray volume of 1500 gal/acre to provide a dosage of 450 gal oil/acre. An untreated control was used for comparison purposes, as well a number of commercially available chemical fungicides applied biweekly according to the manufacturer's instructions. The grasses were rated for visual indication of disease by a trained evaluator.

After about 60 days following treatment, the spray oil was shown to have outperformed many of the comparative chemical treatments, with the spray oil and only one chemical treatment rated as having the little or no indication of disease. Therefore, the spay oil is useful in controlling fungal infections in turfgrass.

Surprisingly, despite the frequent application of a very high dosage of oil, there were no indications of phytotoxicity. As an unexpected result, the turfgrass treated with the oil formulation exhibited more vigorous growth than untreated grass or grass treated with chemicals. Furthermore, the spray oil treated turfgrass had a pleasant residual luster and was not greasy or oily to the touch.

Example 6

Control of Grey Leaf Spot

Experiments were conducted to determine the effect of the spray oil on Grey Leaf Spot in perennial ryegrass turfgrass. The experiments were conducted in the state of Pennsylvania during the summer. A 10% and 20% O/W emulsion was prepared from XPO2 concentrate (see Table 4) and the emulsion was applied to the turfgrass biweekly at a spray volume of 100 gal/acre. An untreated control was used for comparison purposes, as well a commercially available chemical fungicide, Heritage LT, diluted at 0.8 fl oz in 2 gal water. The turfgrass was rated for visual indication of disease based on a scale of 1 to 5, with 5 showing the most indication of disease. The results, as shown in Table 8, demonstrate the spray oil is useful in treating fungal infections in turfgrass.

TABLE 8

Control of Grey Leaf Spot in perennial ryegrass

| | Disease Rating |
|---|---|
| Untreated | 5.0 |
| Heritage LT | 0.3 |
| XPO2, 10% O/W emulsion | 2.3 |
| XPO2, 20% O/W emulsion | 1.7 |

Example 7

Control of Sod Web Worm

Experiments were conducted to determine the effect of the spray oil on sod webworm in St. Augustine turfgrass. The experiment was conducted during the fall in Florida using a 20% O/W emulsion prepared from PC1 concentrate (see Table 4). A commercially available broad spectrum insecticide, Talstar One 0.79 SC (Bifenthrin, made by FMC), as well as an untreated control were also evaluated for comparison purposes. The spray oil O/W emulsion and Talstar were applied at a spray volume of 196 gal/acre (4 gal/1000 sq.ft.) and 88 gal/acre (2 gal/1000 sq.ft.), respectively, then grass blades were excised and placed in a Petri dishes. Five webworm larvae were deposited on the blades in each dish and mortality was determined after a 4 days. Six different sets of experiments were conducted. The averaged results, as shown in Table 9, demonstrate the spray oil is useful as a prophylactic treatment in controlling pests in turfgrass.

TABLE 9

Control of sod webworm in St. Augustine turfgrass

| | Dosage of active ingredient | Mortality % |
|---|---|---|
| Untreated | none | 26.7 |
| PC1 | 34.8 gal oil/acre | 96.7 |
| Talstar | 29.1 oz/acre | 100 |

Example 8

Control of Annual Bluegrass Weevil

Experiments were conducted to determine the effect of the spray oil on Annual bluegrass weevil in a turfgrass mixture of 35% annual bluegrass and 65% bentgrass mowed to 0.5" height. The experiment was carried out in the state of New Jersey in the spring at the Upper Montclair Country Club in the City of Clifton using a 12.5% O/W emulsion of PC1 and PC2 concentrates (see Table 4). Talstar (see Example 7), as well as an untreated control, were also evaluated for comparison purposes. Product was applied to 6 ft² plots at a spray volume of 88 gal/acre (2 gal/1000 sq. ft.) on April 19, May 10, and May 24, with 4 replicate plots for each treatment group. Performance was assessed 14 days after final application by counting the number of annual bluegrass weevil stages in 8 turf sod cores compared to untreated samples. Phytotoxicity was also assessed within 1 week of application and in all cases no perceptible phytotoxicity was observed. The results, as shown in Table 10, demonstrate the spray oil is effective in controlling insect pests in turfgrass.

TABLE 10

Control of Annual Bluegrass Weevil in bluegrass-bentgrass

| | Dosage of active ingredient | % Reduction |
|---|---|---|
| Talstar | 0.1 lb Talstar/acre | 99 |
| PC2 | 11 gal oil/acre | 62 |
| PC1 | 11 gal oil/acre | 71 |
| PC2 + Talstar | 11 gal oil/acre + 0.05 lb Talstar/acre | 97 |

Example 9

Control of Dollar Spot

Experiments were conducted to determine the effect of spray oil on Dollar Spot Disease (caused by the fungus, *Sclerotinia homoeocarpa*) in bentgrass. The experiment was conducted during the summer and fall in Ontario using a 10% emulsions of PC1 (see Table 4). A commercially available fungicide, Daconil 2787 (40% chlorothalonil, made by Syngenta), as well as an untreated control, were also evaluated for comparison purposes. The experimental design consisted of a randomized complete block design with 4 replications, with each plot measuring 1 m×2 m. Treatments were first applied on August 5, and on August 6 the turf was inoculated with *Sclerotinia homoeocarpa*. Treatments were reapplied every two weeks after initial treatment until September 30 using a wheel-mounted compressed air boom sprayer using Lumark 03-F110 nozzles at 140 kPa in water, with a spray volume of 10 litre/100 m² (106 gal/acre) and 11 litre/100 m² (116 gal/acre) for PC1 and Daconil, respectively.

Dollar Spot Disease was evaluated weekly for five weeks after initial treatment by estimating number of infection centres per plot as compared with the control. Phytotoxicity was also evaluated, as indicated by yellowing of the grass. The results, as shown in Table 11, demonstrate that the spray oil is effective in controlling fungal pests in turfgrass.

TABLE 11

Control of dollar spot in bentgrass

| | Dosage of active ingredient | % Reduction Sept. 23 | % Reduction Oct. 7 |
|---|---|---|---|
| PC1 | 10.6 gal/acre | 97 | 95 |
| Daconil 2787 | 2.02 gal/acre | 37 | 63 |

Although preferred embodiments of the invention have been described in some detail herein above, those skilled in the art will recognize that various substitutions and modifications of the invention may be made without departing from the scope of the invention as defined by the claims as defined herein.

The embodiments of the invention for which an exclusive property of privilege is claimed are defined as follows:

1. A method for controlling a turfgrass pest comprising:
applying to turfgrass an oil-in-water emulsion comprising a paraffinic oil and a quick break emulsifier, wherein the oil-in-water emulsion quickly breaks upon application to the turfgrass to release the paraffinic oil from the oil-in-water emulsion, and the oil-in-water emulsion is applied to provide a dosage of paraffinic oil to the turfgrass that is effective for controlling the turfgrass pest; wherein:
the paraffinic oil comprises a paraffin having a carbon number ranging from about C16 to about C35, with an average carbon number of about C23, and the paraffinic oil has a paraffin content of about 99%;
the quick break emulsifier comprises polyoxyethylene lauryl ether, $C_{10}$ to $C_{16}$ alcohol ethoxylates and glycerol oleate;
the weight ratio of the paraffinic oil to the quick break emulsifier is about 99.2:0.8; and
the dosage of paraffinic oil ranges from about 10 gal/acre to about 20 gal/acre;
wherein the turfgrass pest is selected from the group consisting of an insect, a fungus, and a microorganism; and
wherein the oil-in-water emulsion is effective in controlling the turfgrass pests without added synthetic chemical pesticides.

2. The method of claim 1 wherein the turfgrass pest is selected from the group consisting of bluegrass weevils, cutworms, sod webworms, pillbugs, grubs, aphids, mites, chinch bugs, chafers, beetles, grasshoppers, scales, cranefly, earwigs, slugs, ants, fleas, mealybugs, ticks, and causative agents of Grey Leaf Spot, Dollar Spot, Grey Snow Mold, Pink Snow Mold, Brown Patch, Anthracnose, Yellow Turf, Powdery Mildew, *Pythium* Foliar Blight Disease, Necrotic Ring Spot, Pink Patch, Red Thread, Leaf Blight, Yellow Patch, Downey Mildew, *Pythium* Blight, Rusts, Stripe Smut, Summer Leaf Spot, Take-All Patch, and *Microdochium* Patch Disease, and combinations thereof.

3. The method of claim 1 wherein the turfgrass pests are selected from the group consisting of bluegrass weevils, cutworms, sod webworms, mites, and causative agents of Grey Leaf Spot, Dollar Spot, Grey Snow Mold, Pink Snow Mold, Brown Patch, and Anthracnose, and combinations thereof.

4. The method of claim 1 wherein the turfgrass is selected from the group consisting of Fescues, Rye, Bent, Bahia, St. Augustine, Centipede, Kentucky bluegrass, Zoysia Native Grasses, Buffalo grass, Blue Grama, Wheatgrasses, Seashore *Paspalum*, Carpet Grass, Buffo, and Beach Grass, and combinations thereof.

5. The method of claim 1 further comprising preparing the oil-in-water emulsion from about one hour to about two hours prior to the step of applying the oil-in-water emulsion to the turfgrass.

6. The method of claim 1 wherein the oil-in-water emulsion has no phototoxicity phytotoxicity to turfgrass when applied to provide the dosage of paraffinic oil to the turfgrass that is effective for controlling the turfgrass pest.

7. The method of claim 1 wherein the paraffinic oil resides on the turfgrass for a period of not less than one hour.

8. The method of claim 1 wherein the quick break emulsifier comprises an alcohol ethoxylate and glycerol oleate.

9. The method of claim 1 wherein the oil-in-water emulsion comprises a paraffinic oil content ranging from about 1% to about 50% by weight.

10. The method of claim 1 wherein the oil-in-water emulsion comprises a paraffinic oil content ranging from about 10% to about 30% by weight.

11. A method for controlling a turfgrass pest comprising:
applying to turfgrass an oil-in-water emulsion comprising a paraffinic oil and a quick break emulsifier, wherein the oil-in-water emulsion quickly breaks upon application to the turfgrass to release the paraffinic oil from the oil-in-water emulsion, and the oil-in-water emulsion is applied to provide a dosage of paraffinic oil to the turfgrass that is effective for controlling the turfgrass pest; wherein:
the paraffinic oil comprises a paraffin having a carbon number ranging from about C16 to about C35, and the paraffinic oil has a paraffin content of at least about 99%;
the quick break emulsifier comprises polyoxyethylene lauryl ether, an alcohol ethoxylate, or glycerol oleate, or any combination thereof;
the weight ratio of the paraffinic oil to the quick break emulsifier is about 99.1:0.9 to about 99.5:0.5; and
the dosage of paraffinic oil ranges from about 10 gal/acre to about 20 gal/acre;
wherein the turfgrass pest is selected from the group consisting of an insect, a fungus, and a microorganism; and
wherein the oil-in-water emulsion is effective in controlling turfgrass pests without added synthetic chemical pesticides.

12. The method of claim 11 wherein
the oil-in-water emulsion comprises a paraffinic oil content ranging from about 10% to about 30% by weight.

13. The method of claim 12 wherein
the weight ratio of the paraffinic oil to the quick break emulsifier is about 99.2:0.8.

14. The method of claim 11 wherein the turfgrass pest is selected from the group consisting of bluegrass weevils, cutworms, sod webworms, pillbugs, grubs, aphids, mites, chinch bugs, chafers, beetles, grasshoppers, scales, cranefly, earwigs, slugs, ants, fleas, mealybugs, ticks, and causative agents of Grey Leaf Spot, Dollar Spot, Grey Snow Mold, Pink Snow Mold, Brown Patch, Anthracnose, Yellow Turf, Powdery Mildew, *Pythium* Foliar Blight Disease, Necrotic Ring Spot, Pink Patch, Red Thread, Leaf Blight, Yellow Patch, Downey Mildew, *Pythium* Blight, Rusts, Stripe Smut, Summer Leaf Spot, Take-All Patch, and *Microdochium* Patch Disease, and combinations thereof.

15. The method of claim 11 wherein the turfgrass pests are selected from the group consisting of bluegrass weevils, cutworms, sod webworms, mites, and causative agents of Grey Leaf Spot, Dollar Spot, Grey Snow Mold, Pink Snow Mold, Brown Patch, and Anthracnose, and combinations thereof.

16. The method of claim 11 wherein the turfgrass is selected from the group consisting of Fescues, Rye, Bent, Bahia, St. Augustine, Centipede, Kentuky bluegrass, Zoysia Native Grasses, Buffalo grass, Blue Grama, Wheatgrasses, Seashore *Paspalum*, Carpet Grass, Buffo, and Beach Grass, and combinations thereof.

17. The method of claim 11 further comprising preparing the oil-in-water emulsion from about one hour to about two hours prior to the step of applying the oil-in-water emulsion to the turfgrass.

18. The method of claim 11 wherein the oil-in-water emulsion has no phytotoxicity to turfgrass when applied to provide the dosage of paraffinic oil to the turfgrass that is effective for controlling the turfgrass pest.

19. The method of claim 11 wherein the paraffinic oil resides on the turfgrass for a period of not less than one hour.

20. A method for controlling a turfgrass pest comprising:
applying to turfgrass an oil-in-water emulsion comprising a paraffinic oil and a quick break emulsifier, wherein the oil-in-water emulsion quickly breaks upon application to the turfgrass to release the paraffinic oil from the oil-in-water emulsion, and the oil-in-water emulsion is applied to provide a dosage of paraffinic oil to the turfgrass that is effective for controlling the turfgrass pest; wherein:
the paraffinic oil comprises a paraffin having a carbon number ranging from about C16 to about C35, and the paraffinic oil has a paraffin content of at least about 99%;
the quick break emulsifier comprises polyoxyethylene lauryl ether, an alcohol ethoxylate, or glycerol oleate, or any combination thereof;
the weight ratio of the paraffinic oil to the quick break emulsifier is about 99.1:0.9 to about 99.5:0.5; and
the dosage of paraffinic oil ranges from about 2 gal/acre to about 11 gal/acre;
wherein the turfgrass pest is selected from the group consisting of an insect, a fungus, and a microorganism; and
wherein the oil-in-water emulsion is effective in controlling turfgrass pests without added synthetic chemical pesticides.

21. The method of claim 20 wherein the dosage of paraffinic oil ranges from about 2 gal/acre to about 6 gal/acre.

22. The method of claim 20 wherein
the oil-in-water emulsion comprises a paraffinic oil content ranging from about 10% to about 30% by weight.

23. The method of claim 22 wherein
the weight ratio of the paraffinic oil to the quick break emulsifier is about 99.2:0.8.

24. The method of claim 20 wherein the turfgrass pest is selected from the group consisting of bluegrass weevils, cutworms, sod webworms, pillbugs, grubs, aphids, mites, chinch bugs, chafers, beetles, grasshoppers, scales, cranefly, earwigs, slugs, ants, fleas, mealybugs, ticks, and causative agents of Grey Leaf Spot, Dollar Spot, Grey Snow Mold, Pink Snow Mold, Brown Patch, Anthracnose, Yellow Turf, Powdery Mildew, *Pythium* Foliar Blight Disease, Necrotic Ring Spot, Pink Patch, Red Thread, Leaf Blight, Yellow Patch, Downey Mildew, *Pythium* Blight, Rusts, Stripe Smut, Summer Leaf Spot, Take-All Patch, and *Microdochium* Patch Disease, and combinations thereof.

25. The method of claim 20 wherein the turfgrass pests are selected from the group consisting of bluegrass weevils, cutworms, sod webworms, mites, and causative agents of Grey Leaf Spot, Dollar Spot, Grey Snow Mold, Pink Snow Mold, Brown Patch, and Anthracnose, and combinations thereof.

26. The method of claim 20 wherein the turfgrass is selected from the group consisting of Fescues, Rye, Bent, Bahia, St. Augustine, Centipede, Kentuky bluegrass, Zoysia Native Grasses, Buffalo grass, Blue Grama, Wheatgrasses, Seashore Paspalum, Carpet Grass, Buffo, and Beach Grass, and combinations thereof.

27. The method of claim 20 further comprising preparing the oil-in-water emulsion from about one hour to about two hours prior to the step of applying the oil-in-water emulsion to the turfgrass.

28. The method of claim 20 wherein the oil-in-water emulsion has no phytotoxicity to turfgrass when applied to provide the dosage of paraffinic oil to the turfgrass that is effective for controlling the turfgrass pest.

29. The method of claim 20 wherein the paraffinic oil resides on the turfgrass for a period of not less than one hour.

30. The method of claim 20 wherein the quick break emulsifier comprises an alcohol ethoxylate and glycerol oleate.

31. The method of claim 20 wherein the oil-in-water emulsion comprises a paraffinic oil content ranging from about 1% to about 50% by weight.

\* \* \* \* \*

UNITED STATES PATENT AND TRADEMARK OFFICE
CERTIFICATE OF CORRECTION

PATENT NO.        : 8,747,874 B2                                    Page 1 of 2
APPLICATION NO.   : 12/563929
DATED             : June 10, 2014
INVENTOR(S)       : Michael Fefer It is certified that error appears in the above-identified patent and that said Letters Patent is hereby corrected as shown below:

On the Title Page:

Page 2, Col. 2 (Other Publications), line 12, delete "rersistance" and insert -- resistance --

Page 2, Col. 2 (Other Publications), line 49, delete "Agriculture2004" and insert -- Agriculture 2004 --

Page 3, Col. 2 (Other Publications), line 13, delete "PCT/CA2007/001762." and insert -- PCT/CA2007/001762, 2007. --

Page 3, Col. 2 (Other Publications), line 14-15, delete "PCT/CA2007/001762." and insert -- PCT/CA2007/001762, 2007. --

Page 3, Col. 2 (Other Publications), line 55, delete "2006." and insert -- 5/2006. --

Page 4, Col. 1 (Other Publications), line 4, delete "comell." and insert -- cornell. --

Page 4, Col. 1 (Other Publications), line 60, delete "conn" and insert -- com --

Page 4, Col. 2 (Other Publications), line 7, delete "Landscae" and insert -- Landscape --

Page 5, Col. 1 (Other Publications), line 26, delete "CropScienc" and insert -- CropScience --

In the Claims:

Col. 12, line 67, Claim 4, delete "Kentuky" and insert -- Kentucky --

Col. 13, line 9, Claim 6, after "no" delete "phototoxicity"

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,747,874 B2

Col. 13, line 45, Claim 11, delete "turfgrass" and insert -- the turfgrass --

Col. 14, line 5, Claim 16, delete "Kentuky" and insert -- Kentucky --

Col. 14, line 41, Claim 20, delete "turfgrass" and insert -- the turfgrass --

Col. 15, line 3, Claim 26, delete "Kentuky" and insert -- Kentucky --

UNITED STATES PATENT AND TRADEMARK OFFICE
CERTIFICATE OF CORRECTION

| | | |
|---|---|---|
| PATENT NO. | : 8,747,874 B2 | Page 1 of 1 |
| APPLICATION NO. | : 12/563929 | |
| DATED | : June 10, 2014 | |
| INVENTOR(S) | : Fefer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this
Twenty-fifth Day of August, 2015

Michelle K. Lee
*Director of the United States Patent and Trademark Office*